United States Patent

Weiss et al.

Patent Number: 6,019,774
Date of Patent: Feb. 1, 2000

[54] CARPAL TUNNEL RELEASE APPARATUS AND METHOD

[75] Inventors: Arnold Peter Weiss; Edward Akelman, both of Barrington, R.I.; Michael S. Collins, San Diego, Calif.

[73] Assignee: Kinetikos Medical Incorporated, San Diego, Calif.

[21] Appl. No.: 09/208,706

[22] Filed: Dec. 10, 1998

[51] Int. Cl.[7] .................................................. A61B 17/32
[52] U.S. Cl. .......................................................... 606/167
[58] Field of Search ..................................... 606/167, 168, 606/169, 170, 171; 30/294

[56] References Cited

U.S. PATENT DOCUMENTS 4,026,295 5/1977 Lieberman ............................... 606/167

*Primary Examiner*—Michael Buiz
*Assistant Examiner*—Tan-Uyen T. Ho
*Attorney, Agent, or Firm*—Jenkins & Wilson, P.A.

[57] ABSTRACT

A carpal tunnel release apparatus and method including a surgical knife including an elongated handle having a forward portion and a rearward portion with the forward portion of the handle terminating in a cutting head. The cutting head has top edge and a bottom edge with the cutting head terminating in a substantially linear cutting edge extending from proximate the bottom edge of the cutting head toward the top edge of the cutting head. The cutting edge intersects and forms an angle with an upper guide finger which is the only structure which projects forwardly past the plane of the cutting edge and which at least partially forms the top edge of the cutting head. The guide apparatus includes an elongated bar defining one or more elongated grooves therein. A bottom portion of the forward portion of the knife is at least partially receivable within the groove of the guide member such that lateral movement of the forward portion is substantially restricted and such that the forward portion of the handle is slidably movable forward or backward while guided within the groove.

13 Claims, 6 Drawing Sheets

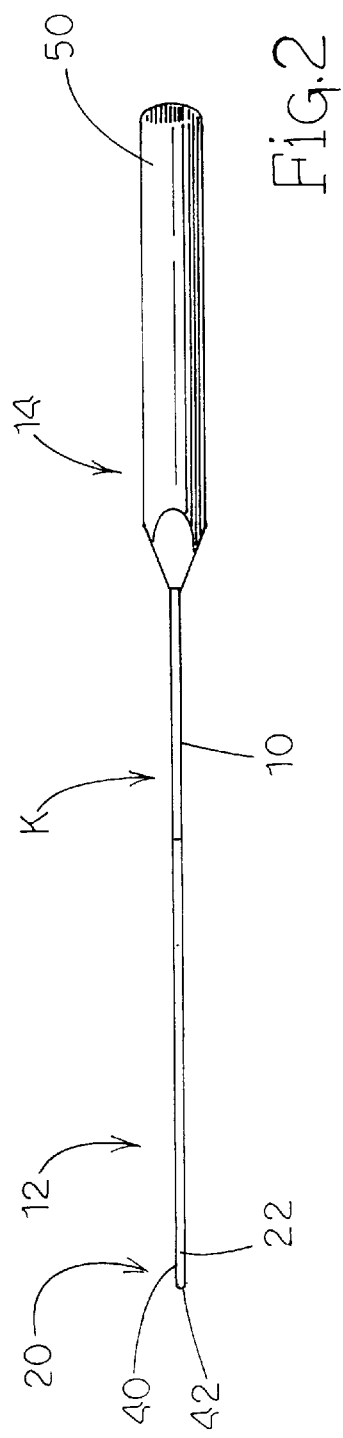
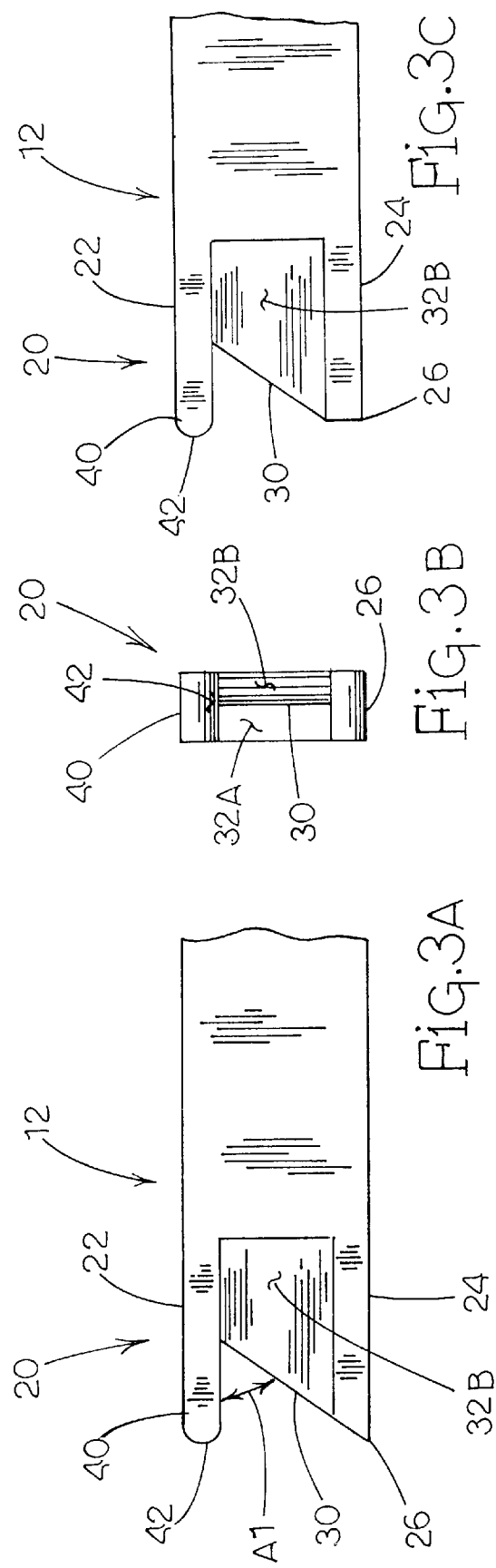

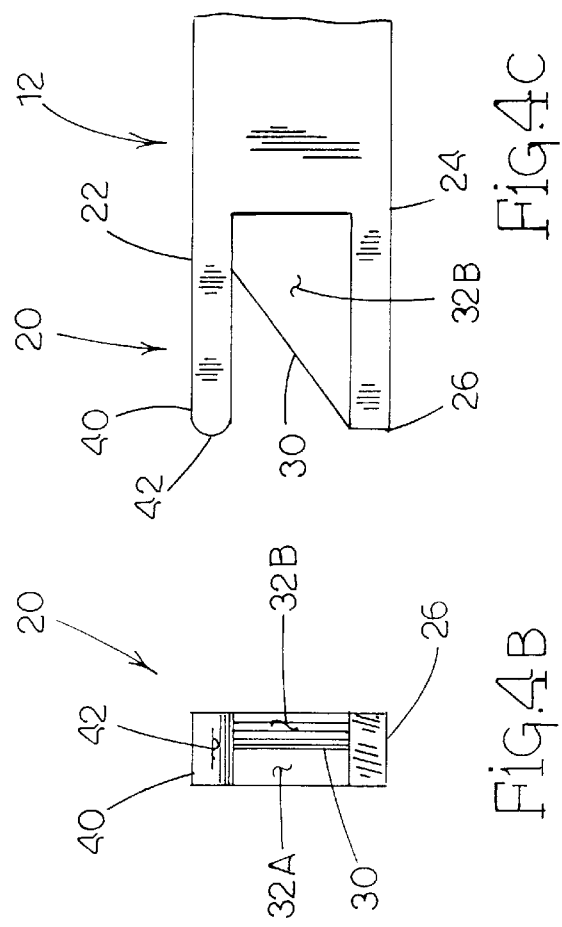

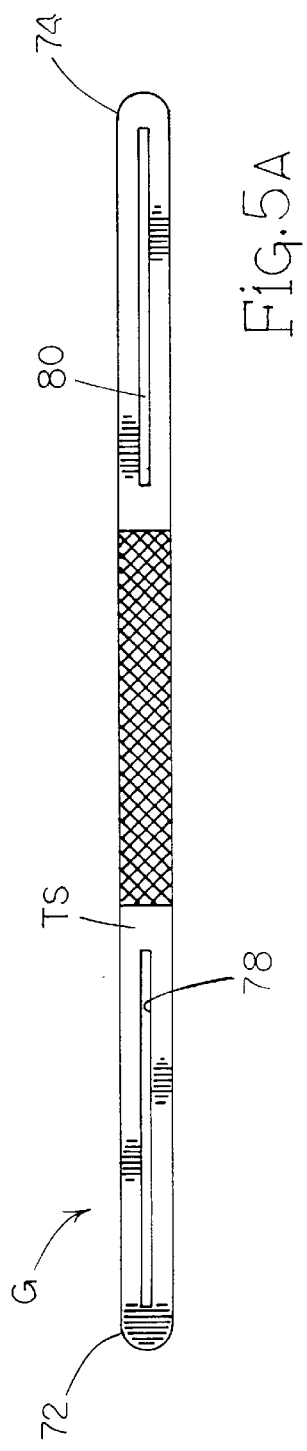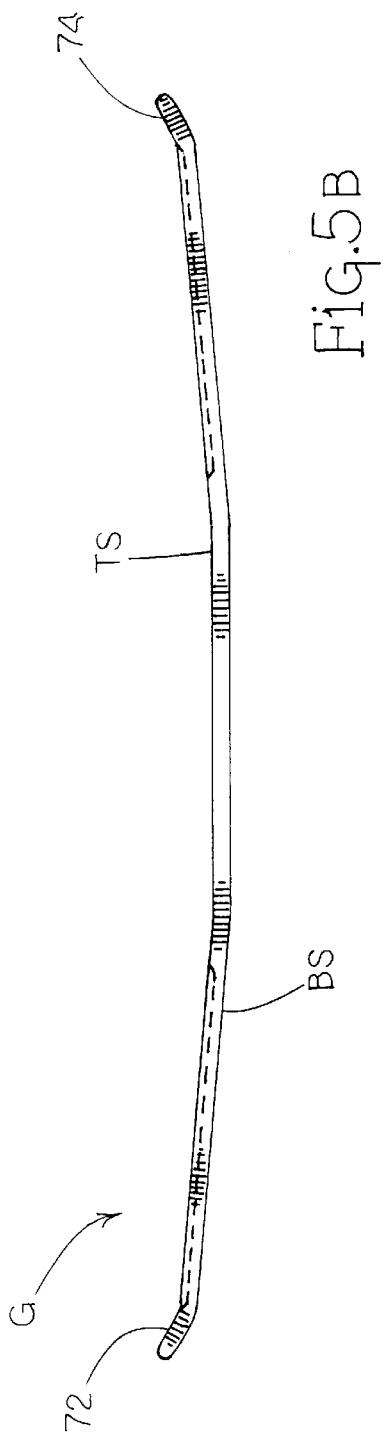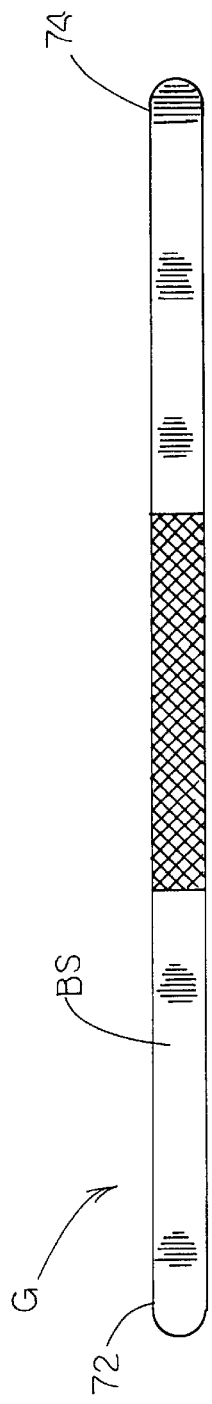

CARPAL TUNNEL RELEASE APPARATUS AND METHOD

TECHNICAL FIELD

The present invention relates generally to surgical apparatuses and methods, and more particularly, to carpal tunnel release surgical apparatuses and methods.

BACKGROUND ART

There are a variety of apparatuses and methods designed for use in performing carpal tunnel release surgery. Carpal tunnel syndrome is a commonly known problem resulting from compression of the median nerve within the carpal tunnel in the hand which is the name for an anatomic passageway in the wrist and palm. Conditions that crowd or reduce the size of the carpal tunnel and initiate symptoms associated with carpal tunnel syndrome, which is typically characterized by some combination of wrist pain, forearm aching, and/or pain, tingling and numbness in the index and middle fingers as well as the thumb. It is typical for middle-aged people whose jobs necessitate repeated exposure to certain movements and/or vibrating tools, such as those which can be experienced by utilizing computer keyboards, typewriters as well as work which can be associated with assembly lines to experience carpal tunnel syndrome.

It is well known that when carpal tunnel syndrome symptoms become persistent and progressive, division of the deep transverse carpal ligament is often recommended for treatment. A variety of apparatuses and methods for surgically releasing the transverse carpal ligament have been developed and are known in the art. Examples of such apparatuses and methods include, for example, U.S. Pat. No. 5,334,214 to Putnam which discloses a guidance mechanism and cuffing mechanism for subcutaneous insertion in spaced-apart incisions for dividing the transverse carpal ligament. The guidance mechanism is placed below the transverse carpal ligament, and the cutting mechanism is placed above the transverse carpal ligament. The guidance mechanism forms a slot adapted to receive a portion of the cutting mechanism such that as the cuffing mechanism is advanced, it is guided by the guidance mechanism with a portion of the cuffing mechanism sliding through and fitted within the slot of guidance mechanism as a knife portion of the cutting mechanism divides a carpal tunnel ligament.

U.S. Pat. No. 5,387,222 to Strickland discloses a carpal tunnel tome method for performing carpal tunnel release surgery. The disclosed tome includes a slender handle with a blade at one end thereof, with the blade being bounded on both sides by a pair of relatively blunt protuberances extending distally beyond the cutting edge of the blade. The protuberances allow the instrument to straddle a carpal tunnel ligament and serve to protect surrounding tissue during the cutting procedure. Similarly, U.S. Pat. No. 5,507,800, also to Strickland, discloses the carpal tunnel tome disclosed by U.S. Pat. No. 5,387,222, but is directed to coverage of the apparatus itself whereas U.S. Pat. No. 5,387,222 is directed toward coverage of the methodology. In the surgical procedure for the carpal tunnel tome of U.S. Pat. Nos. 5,387,222 and 5,507,800, an incision is initially made in a patient's palm adjacent the distal edge of the transverse carpal ligament. The incision and underlying adipose tissue are then retracted until the distal portion of the transverse carpal ligament becomes visible. Next, the carpal tunnel tome with the blade shielded on its ends by the pair of blunt protuberances projecting away from the blade is positioned in the incision such that the protuberances straddle the transverse carpal ligament and the blade is positioned against the ligament. The carpal tunnel tome is then advanced toward the patient's wrist until the transverse carpal ligament becomes completely divided. Finally, the carpal tunnel tome is withdrawn from the patient, and the incision is typically closed with a few sutures.

U.S. Pat. No. 5,413,580 to Stephenson discloses a similar carpal tunnel knife which includes an elongated shaft with a handle mounted on the rearward end of the shaft and oriented perpendicularly thereto. The forward end of the shaft includes a generally planar blade portion which is oriented perpendicularly with respect to the handle. This blade portion includes a pair of forwardly projecting guide fingers which are separated by a notch, and a cutting edge formed within the notch and extending between the guide fingers.

As illustrated by the exemplary patents described above, a method which is common in the art of carpal tunnel surgery involves making a relatively shorter incision located entirely in the palm and then dividing the deep transverse carpal ligament utilizing a knife which includes protuberances or guide fingers on both sides of the knife. The knife is passed proximately toward a patient's wrist for complete division of the transverse carpal ligament, and this step of cutting the transverse carpal ligament is recognized as causing danger of inadvertent injury to the median nerve or other structures within the hand as the knife is passed proximately during the cutting method.

In view of the above, and despite the existence of a variety of apparatuses and methods for carpal tunnel release surgery, there remains much room for improvement in the art, particularly for a carpal tunnel release apparatus and method which is simple, safe and effective for complete division of the transverse carpal ligament in an effort to minimize pain and recovery time.

DISCLOSURE OF THE INVENTION

In accordance with the present invention, a carpal tunnel release apparatus and method are provided. The apparatus comprises a surgical knife for performing carpal tunnel release surgery wherein the knife includes an elongated handle having a forward portion and a rearward portion with the forward portion of the handle terminating in a cutting head. The cutting head has top edge and a bottom edge with the cutting head terminating in a substantially linear cutting edge extending from proximate the bottom edge of the cutting head toward the top edge of the cutting head. The cutting edge intersects and forms an angle with an upper guide finger which is the only structure which projects forwardly past the plane of the cutting edge and which at least partially forms the top edge of the cutting head. In a preferred embodiment, the cutting edge and the guide finger form an angle of less than approximately ninety (90) degrees. The apparatus according to the present invention additionally includes a guide apparatus comprising an elongated bar defining an elongated groove therein. A bottom portion of the forward portion of the knife is at least partially receivable within the groove of the guide member such that lateral movement of the forward portion is substantially restricted and such that the forward portion of the handle is slidably movable forward or backward while guided within the groove.

Also in accordance with the present invention, the method for cutting a transverse carpal ligament is provided utilizing the apparatuses described hereinabove. In a preferred embodiment, the method according to this invention comprises the initial step of appropriately administering anesthesia to a patient's hand. A small surgical incision is then made on the palmar skin coursing through the palmar fascia to the transverse carpal ligament at its distal portion. Under direct vision, the distal portion of the transverse carpal ligament is then incised longitudinally as far proximately as possible. Next, an end of the guide apparatus is passed underneath the remaining portion of the transverse carpal ligament proximately through the distal incised portion with the curved tip of the guide apparatus passing proximately in contact with the under surface of the transverse carpal ligament until the guide apparatus reaches beyond the proximal extent of the ligament itself. After appropriate passage of the guide apparatus below the transverse carpal ligament, the surgical knife is engaged into the guide groove and passed proximately to cut the transverse carpal ligament until complete division and release of the remaining transverse carpal ligament occurs.

It is therefore an object of the present invention to provide a novel carpal tunnel release apparatus and method.

It is another object of the present invention to provide a carpal tunnel release apparatus and method which can safely and effectively be utilized for releasing the transverse carpal ligament with minimum risk to the median nerve or other structures.

Some of the objects of the invention having been stated hereinabove, other objects will become evident as the description proceeds, when taken in connection with the accompanying drawings as best described hereinbelow.

BRIEF DESCRIPTION OF THE DRAWINGS

FIG. 2 of the drawings is an isolated top plan view of the surgical knife of the present invention;

FIG. 3A of the drawings is a side elevation view of a forward portion of the surgical knife of the present invention including one embodiment of the cutting head thereof;

FIG. 3B of the drawings is a front end view of the cutting head shown in FIG. 3A;

FIG. 3C of the drawings is a side elevation view of the forward portion of the surgical knife of the present invention shown in FIG. 3A wherein a portion of the cutting head has an alternative configuration;

FIG. 4A of the drawings is a side elevation view of a forward portion of the surgical knife of the present invention including a second embodiment of the cutting head;

FIG. 4B of the drawings is a front end view of the cutting head shown in FIG. 4A;

FIG. 4C of the drawings is a side elevation view of the forward portion of the surgical knife of the present invention shown in FIG. 4A wherein a portion of the cutting head has an alternative configuration;

FIGS. 5A, 5B and 5C of the drawings are a top plan view, a side elevation view, and a bottom plan view, respectively, of the guide apparatus of the present invention.

DETAILED DESCRIPTION OF THE PREFERRED EMBODIMENT

Figure 1:
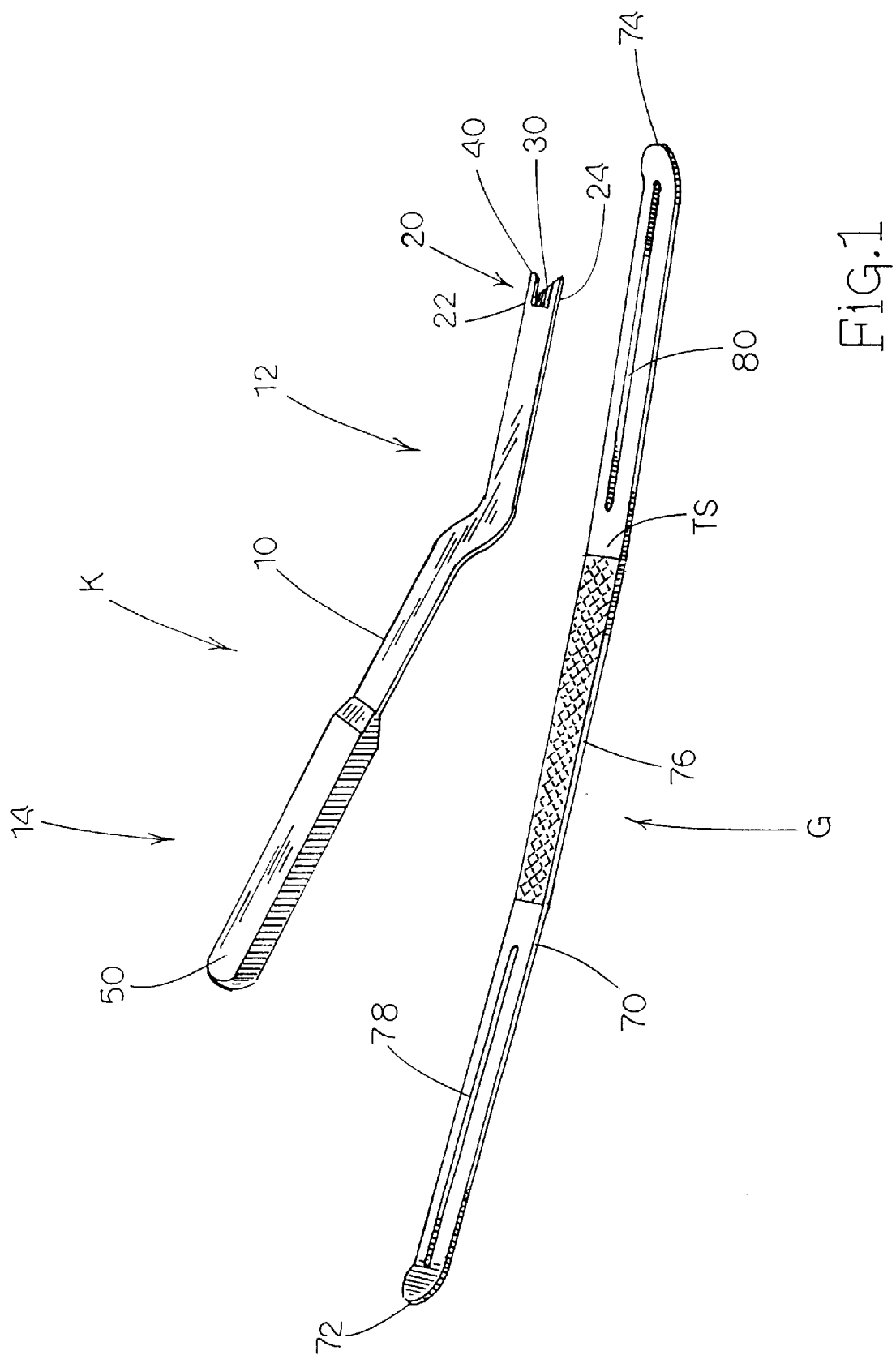
FIG. 1 of the drawings is a perspective view of the surgical knife and guide apparatus according to the present invention.

A novel carpal tunnel release apparatus and method are provided in accordance with the present invention. The apparatus comprises a surgical knife generally designated K and a guide apparatus generally designated G as shown in FIG. 1 of the drawings. As can be appreciated by those of skill in the art, knife K and guide apparatus G are preferably constructed of stainless steel, but can be constructed of any material suitable for use as described herein.

Knife K is designed for performing carpal tunnel release surgery and includes an elongated handle 10 with a forward portion generally designated 12 and a rearward portion generally designated 14, as shown in FIG. 1. Forward portion 12 terminates in a cutting head generally designated. Cutting head 20 defines an upper edge 22 and a bottom edge 24. Cutting head 20 terminates in a cutting edge 30 which extends from proximate bottom edge 24 toward top edge 22 of cutting head 20 such that cutting edge 30 intersects and forms an angle with an upper guide finger 40 which projects forwardly past cutting edge 30, as described in further detail hereinbelow. Knife K will be described in further detail hereinbelow.

Still referring to FIG. 1, rearward portion 14 of handle 10 most preferably includes a grip 50 thereon suitable for gripping knife K for carpal tunnel release surgery as described hereinbelow. While it is envisioned according to the present invention that the shape of handle 10 can be of other suitable configurations for carpal tunnel release surgery, handle 10 preferably is of a configuration as illustrated in FIG. 1 of the drawings wherein handle 10 is bent or angled between forward portion 12 and rearward portion 14. In this configuration, grip 50 on rearward portion 14 of handle 10 forms an angle of slightly less than 180 degrees (180°) with forward portion 12 of handle 10.

Guide apparatus G of the present invention is also shown in FIG. 1 of the drawings and comprises an elongated bar 70 which is substantially flat on its upper side and terminates in opposite ends 72 and 74 which are preferably slight curved. Ends 72 and 74 can be different sizes and/or shapes or can be identical in accordance with the present invention. Bar 70 defines a gripping surface 76 as illustrated in FIG. 1 of the drawings, and bar 70 also preferably defines a pair of grooves 78 and 80, which can be identical or different, positioned on the upper side of bar 70 on opposite sides of gripping surface 76. Bar 70 is described in further detail hereinbelow.

In FIG. 2 of the drawings, an isolated, top plan view of the knife K is illustrated as handle 10 is shown having forward portion 12 and rearward portion 14 wherein grip 50 is positioned on the end of rearward portion 14. Also as illustrated in FIG. 2, forward portion 12 of handle 10 terminates in cutting head 20 which comprises top edge 22 and guide finger 40 as shown in the top plan view of FIG. 2. Guide finger 40 terminates preferably in rounded terminal end 42.

An isolated view of a portion of forward portion 12 of handle 10 is illustrated in FIG. 3A of the drawings which best illustrates one embodiment of cuffing head 20 according to the present invention. As shown, cutting head 20 includes bottom edge 24 and top edge 22 which terminates in rounded guide finger 40 (which terminates in rounded terminal end 42). The middle portion of cutting head 20 terminates in a cutting edge 30 which is preferably linear and extends from proximate bottom edge 24 to proximate top edge 22.

Cutting edge 30 is preferably a double-beveled sharp cutting edge resulting from the terminal point of intersection of tapering cutting sides 32A and 32B, best illustrated in FIG. 3B of the drawings. Cutting head 20 is configured such that cutting edge 30 intersects and forms an angle A1 with upper guide finger 40. Angle A1 formed between cutting edge 30 and guide finger 40 is desirably approximately 90 degrees (90°) or less, and in the preferred embodiment illustrated in FIG. 3A of the drawings, angle A1 formed between cutting edge 30 and upper guide finger 40 is approximately 55 degrees (55°). Although it is envisioned according to this invention that cutting edge 30 could extend from its intersection with upper guide finger 40 all the way to terminal end 26 of bottom edge 24, it is preferred in accordance with this invention that cutting edge 30, and cutting sides 32A and 32B, stop short from terminal end 26 of bottom edge 24, as shown in the various figures of drawings.

As shown in FIG. 3A of the drawings and in accordance with the present invention, only guide finger 40 extends or projects beyond the plane defined by cutting edge 30 as terminal end 26 of bottom edge 24 is illustrated in FIG. 3A as on th e plane of cutting edge 30 and not projecting beyond the plane of cutting edge 30. In this embodiment, rounded terminal end 42 of upper guide finger 40 and terminal end 26 of bottom edge 24 both terminate straight across from one another as both extend distally an identical distance. Alternatively, terminal end 26 of bottom edge 24 can stop short of and be behind the plane defined by cutting edge 30 such as in the configuration shown in FIG. 3C of the drawings wherein terminal end 26 of bottom edge 24 does not extend all the way to or beyond the plane of cutting edge 30.

A second embodiment of cutting head 20 according to the present invention is illustrated in FIGS. 4A and 4B of the drawings with the only difference being that the angle formed at the intersection of upper guide finger 40 and cutting edge 30, which is designated angle A2, is approximately 35 degrees (35°). Rounded terminal end 42 of upper guide finger 40 and terminal end 26 of bottom edge 24 continue to both terminate straight across from one another as both extend identical distances distally. FIG. 4C of the drawings illustrates the embodiment of cutting head 20 shown in FIGS. 4A and 4B of the drawings with terminal end 26 of bottom edge 24 terminating short of and being behind the plane defined by cutting edge 30 similar to FIG. 3C discussed hereinabove.

Referring now to FIGS. 5A, 5B and 5C of the drawings which illustrate guide apparatus G of the present invention, guide apparatus G comprises an elongated member or bar 70 having opposite curved ends 72 and 74, one preferably larger than the other. Bar 70 has a top side TS and a bottom side BS which are best illustrated in FIGS. 5A and 5C, respectively. On both top side TS and bottom side BS, gripping surface GS is defined by bar 70 between curved ends 72 and 74. On its top side TS, bar 70 preferably defines a pair of grooves 78 and 80 which are positioned on opposite sides of gripping surface 76 of bar 70.

In accordance with the present invention, grooves 78 and 80 are elongated and extend on top surface TS of bar 70 from proximate gripping surface 76 to proximate an end (72 or 74) of bar 70. Grooves 78 and 80 can be of identical depths and lengths defined on top side TS of bar 70, and grooves 78 and 80 are designed for receiving therein a bottom portion of cutting head 20 of knife K, such as for receiving at least terminal end 26 and a portion of bottom edge 24 of cutting head 20, during carpal tunnel release surgery as described further hereinbelow. Bar 70 is preferably slightly curved along its length, as best illustrated in the side view illustration of FIG. 5B, and designed for passage underneath the transverse carpal ligament during carpal tunnel release surgery as described further hereinbelow.

Focusing now on the method of the present invention utilizing knife K and guide apparatus G for carpal tunnel release surgery, the method according to this invention can be broken down and described by various steps discussed as follows.

Step 1 according to the method of the present invention (not shown) utilizing knife K and guide apparatus G comprises, as can be appreciated by those of skill in the art, appropriate administration of suitable anesthesia to the palm of a patient. In a preferred embodiment, ten (10) cc of anesthetic mixture (5 cc of 1% lidocaine without epinephrine plus 5 cc of 0.25% marocaine without epinephrine) is injected into the midline of the proximal palm to the proximal wrist crease of a patient. The anesthesia should infiltrate both the carpal tunnel and subcutaneous tissues while being careful not to injure the median nerve.

Figure 6A:
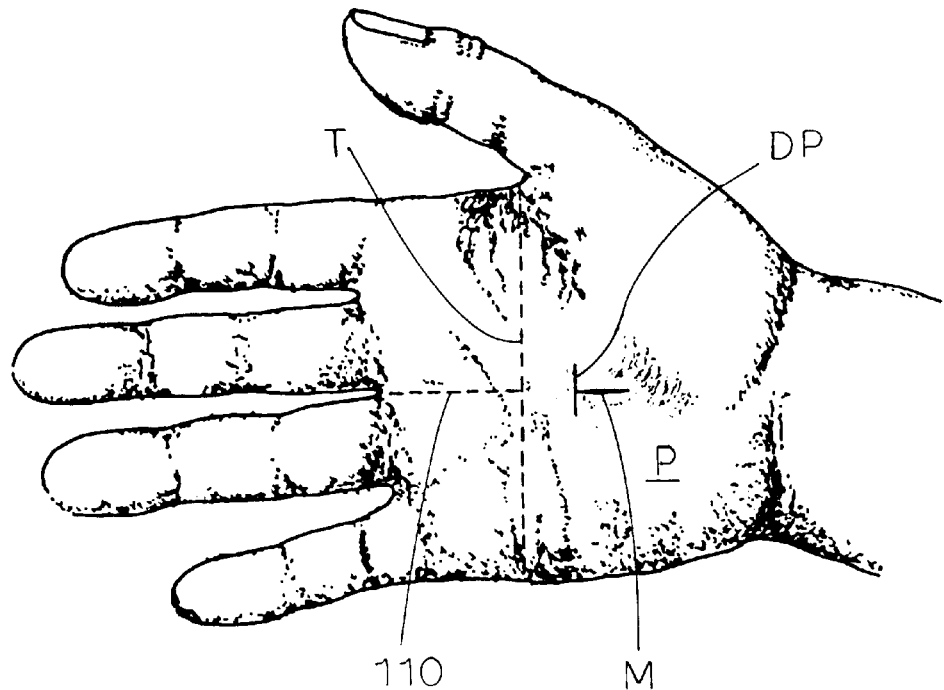
FIGS. 6A–6D of the drawings are perspective views of the carpal tunnel surgical release method of the present invention utilizing the surgical knife and guide apparatus.

For Step 2 of the method of the present invention, and referring specifically to FIG. 6A of the drawings, a transverse line 100 is drawn from the proximal-most extent of the first web space in palm P of the hand of the patient. A second line 110 is then drawn longitudinally from the radial border of the ring finger proximally. A point 0.5 to 1 cm proximal to the junction of transverse line 100 and second line 110 represent the distal point line, designated DP, of the surgical incision to be made. From distal point DP, a 1.5–2 cm surgical incision mark M should be drawn in a longitudinal fashion proximally.

Figure 6B:
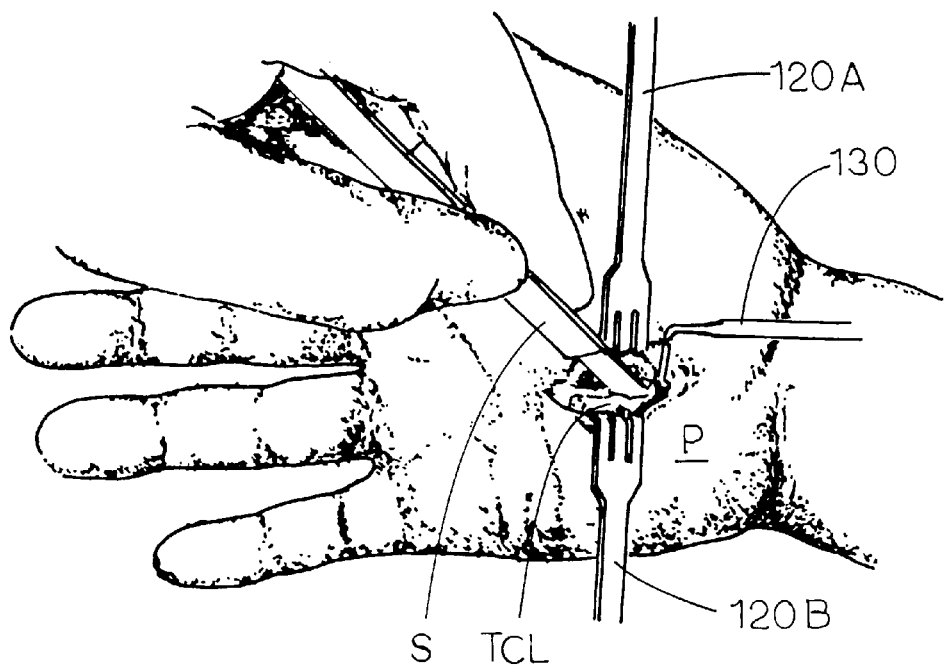

For Step 3 of the method of the present invention, and after tourniquet exsanguination of the upper extremity, a No. 15 blade of a scalpel, such as scalpel S shown in FIG. 6B, preferably is utilized to incise the palmar skin along mark M coursing through the palmar fascia to the transverse carpal ligament at its distal portion. This step should be carefully accomplished without damaging the vascular arch. Utilizing either a self-retaining retractor or two Senn retractors, such as those shown as 120A and 120B of FIG. 6B, and one Ragnell retractor, such as 130 shown in FIG. 6B, the distal portion of transverse carpal ligament TCL is identified.

For Step 4 of the method of the present invention, and referring specifically to FIG. 6B of the drawings, the distal portion of transverse carpal ligament TCL is incised under direct vision longitudinally as far proximally as possible utilizing a blade, such as No. 15 blade of scalpel S and also utilizing proximal Ragnell retractor 130 for visualization.

Figure 6C:
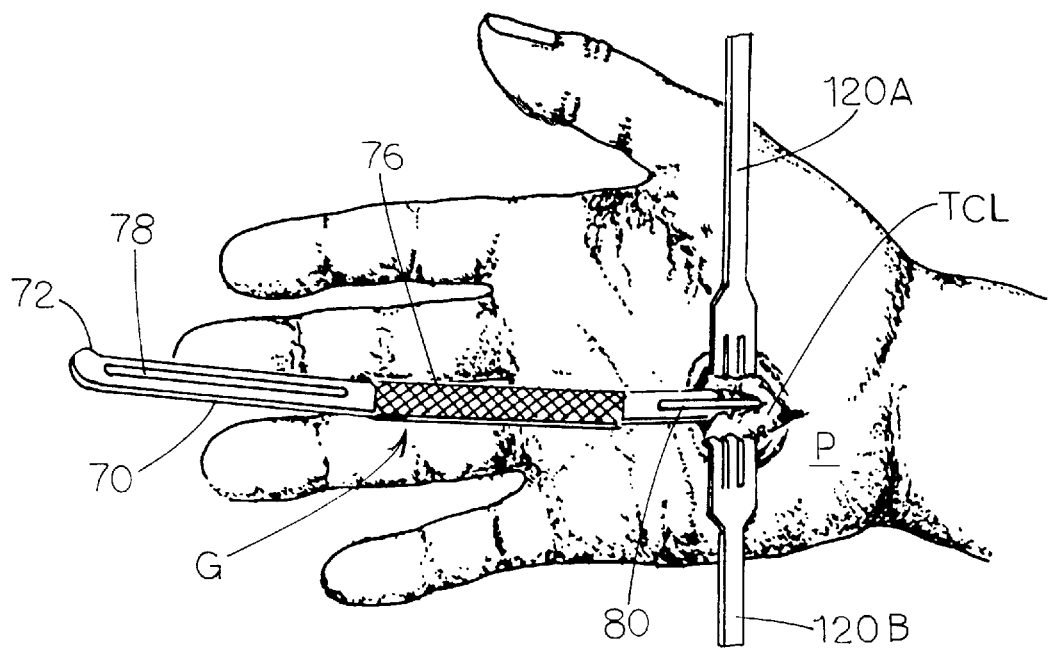

In Step 5 of the method of the present invention, and referring specifically to FIG. 6C of the drawings, an end, such as end 74 of guide apparatus G is then passed underneath the remaining portion of transverse carpal ligament TCL proximally through the distal incised portion with top side TS facing upwardly. The curved tip of the end 74 of guide apparatus G should pass proximately always in contact with the under surface of transverse carpal ligament TCL until the end of guide apparatus G reaches at least location designated L wherein it is beyond the proximal extent of transverse carpal ligament TCL itself. As shown in FIG. 4, the end of guide apparatus G should extend all the way to location L.

Figure 6D:
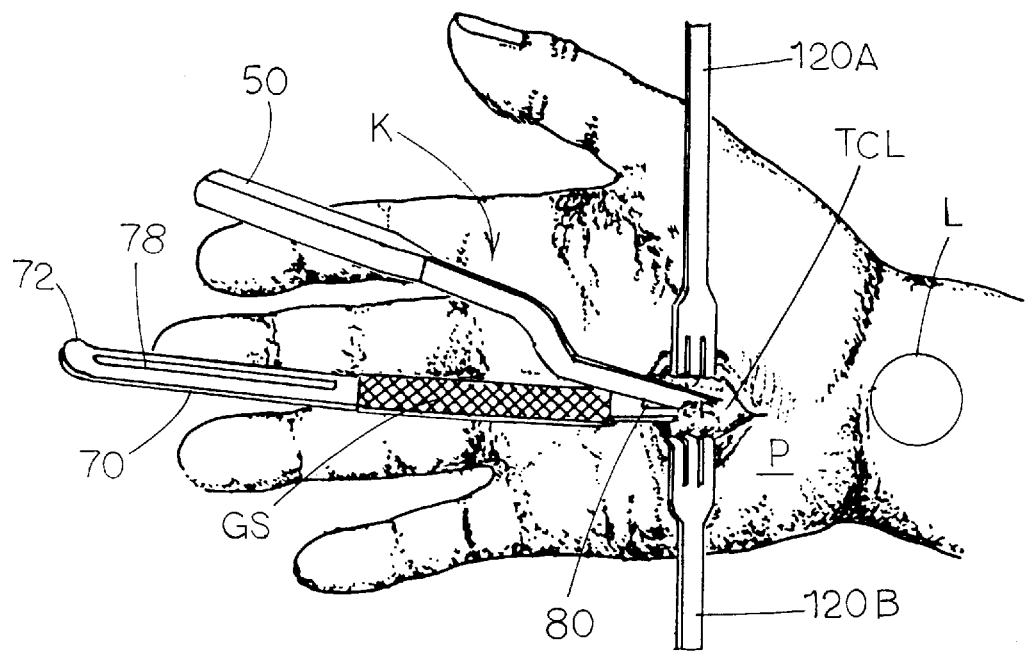

In Step 6 according to the method of the present invention, and referring specifically to FIG. 6D of the drawings, while guide apparatus G is maintained in position snugly against the bottom surface of transverse carpal ligament TCL and after ensuring appropriate passage of guide apparatus G beneath transverse carpal ligament TCL (without tissues between transverse carpal ligament TCL and guide apparatus G itself), knife K can then be utilized. At least a portion of cutting head 20 of knife K is engagedly positioned within a groove, such as groove 80, of guide apparatus G wherein cutting head 20 can be positioned such that advancement of knife K allows transverse carpal ligament TCL to be strategically positioned for cutting between guide finger 40 and guide apparatus G. Once in this position, knife K is advanced or passed proximally while guide apparatus G is maintained in its position such that transverse carpal ligament TCL is cut by cutting edge 30 of knife K in order to completely release the remaining portion of transverse carpal ligament TCL. During advancement of knife K, the portion of knife K within groove 80 at least substantially restricts lateral movement thereof and allows knife K to be suitably guided for cutting only transverse carpal ligament TCL with minimal risk of accidentally cutting other structures or tissues such as the median nerve, as can be appreciated by those of skill in the art. After complete and suitable cutting by knife K of transverse carpal ligament TCL, knife K can then be retracted, and guide apparatus G can be utilized to bluntly probe transverse carpal ligament TCL to ensure its complete release.

For the final step according to the method of the present invention, Step 7 comprises appropriately irrigating the wound and utilizing nylon sutures, preferably two (2), for proper wound closure. A soft, short palmar dressing can then be placed on the wound, ensuring that full finger and thumb flexion and extension can occur, without difficulty, post-operatively. Patients are encouraged to perform range-of-motion exercises post operatively, although heavy lifting should be avoided. The sutures can typically be removed at 7 to 10 days with progressive increases in hand use counseled for the patient over the ensuing weeks.

It can therefore be seen that the present invention provides a novel carpal tunnel release apparatus and method. It can further be seen that the present invention provides a carpal tunnel release apparatus and method which can safely and effectively be utilized for releasing the transverse carpal ligament with minimum risk to the median nerve or other structures.

It will be understood that various details of the invention may be changed without departing from the scope of the invention. Furthermore, the foregoing description is for the purpose of illustration only, and not for the purpose of limitation, as the invention is defined by the following, appended claims.

What is claimed is:

1. A surgical knife apparatus for performing carpal tunnel release surgery, said knife apparatus comprising:
    (a) an elongated handle having a forward portion and a rearward portion with said forward portion of said handle terminating in a cutting head; and
    (b) said cutting head having a top edge and a bottom edge, and said cutting head terminating in a substantially linear cutting edge extending from proximate said bottom edge of said cutting head toward said top edge of said cutting head, and said cutting edge intersecting and forming an angle with an upper guide finger which projects forwardly past said cutting edge and which at least partially forms said top edge of said cutting head.

2. The knife apparatus of claim 1 wherein said cutting edge and said guide finger form an angle of less then approximately ninety (90) degrees.

3. The knife apparatus of claim 1 wherein said guide finger and a terminal end of said bottom edge of said cutting head extends substantially identical distances distally.

4. The knife apparatus of claim 1 wherein a terminal end of said guide finger is rounded.

5. The knife apparatus of claim 1 wherein said rearward portion of said handle forms an angle of less than approximately one hundred eighty (180) degrees with said forward portion of said handle.

6. The knife apparatus of claim 5 wherein said rearward portion of said handle includes a grip.

7. A surgical knife and guide apparatus for performing carpal tunnel release surgery, said knife and guide apparatus comprising:
    (a) an elongated handle having a forward portion and a rearward portion with said forward portion terminating in a cutting head;
    (b) said cutting head of said handle having a top edge and a bottom edge, and said cutting head terminating in a substantially linear cutting edge extending from proximate said bottom edge of said cutting head toward said top edge of said cutting head, and said cutting edge intersecting and forming an angle with an upper guide finger which projects forwardly past said cutting edge and which at least partially forms said top edge of said cutting head; and
    (c) an elongated guide member defining an elongated groove therein, with said forward portion of said handle being at least partially receivable within said groove of said guide member such that lateral movement of at least a portion of said forward portion is substantially restricted and such that said forward portion of said handle is slidably movable forward or backward within said groove.

8. The knife and guide apparatus of claim 7 wherein said cutting edge and said guide finger form an angle of less then approximately ninety (90) degrees.

9. The knife apparatus of claim 7 wherein said guide finger extends forwardly a distance substantially identical to a distance that said cutting edge extends forwardly.

10. The knife apparatus of claim 7 wherein a terminal end of said guide finger is rounded.

11. The knife apparatus of claim 7 wherein said rearward portion of said handle includes a gripping portion which forms an angle of less than approximately one hundred eighty (180) degrees with said forward portion of said handle portion.

12. A method of cutting a transverse carpal ligament, said method comprising the steps of:
    (a) providing a surgical knife and guide apparatus comprising:
        (i) an elongated handle having a forward portion and a rearward portion with said forward portion terminating in a cutting head;
        (ii) said cutting head of said handle having a top edge and a bottom edge, and said cutting head terminating in a substantially linear cutting edge extending from proximate said bottom edge of said cutting head toward said top edge of said cutting head, and said cutting edge intersecting and forming an angle with an upper guide finger which projects forwardly past said cutting edge and which at least partially forms said top edge of said cutting head; and
        (iii) an elongated guide member defining an elongated groove therein, with said forward portion of said handle being at least partially receivable within said groove of said guide member such that lateral movement of said forward portion is substantially restricted and such that said forward portion of said handle is slidably movable forward or backward within said groove;

(b) positioning said guide member adjacent a transverse carpal ligament with said groove of said guide member substantially facing said ligament;
(c) positioning said forward portion of said handle of said knife at least partially within said groove of said guide member; and
(d) cutting said ligament by advancing said handle of said knife forward to cut said ligament with said cutting edge while said forward portion of said handle remains at least partially received within said groove of said guide member.

13. The method of claim 12 wherein said guide finger advances above said ligament during the cutting step of paragraph (d).

* * * * *